US009704018B2

(12) United States Patent
Yoshihara et al.

(10) Patent No.: US 9,704,018 B2
(45) Date of Patent: Jul. 11, 2017

(54) INFORMATION PROCESSING APPARATUS, INFORMATION PROCESSING SYSTEM, INFORMATION PROCESSING METHOD, PROGRAM, AND RECORDING MEDIUM

(71) Applicants: Yoshiko Yoshihara, Tokyo (JP); Tomoharu Kiyuna, Tokyo (JP)

(72) Inventors: Yoshiko Yoshihara, Tokyo (JP); Tomoharu Kiyuna, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 14/607,766

(22) Filed: Jan. 28, 2015

(65) Prior Publication Data

US 2015/0147772 A1 May 28, 2015

Related U.S. Application Data

(62) Division of application No. 13/824,228, filed as application No. PCT/JP2011/071931 on Sep. 27, 2011, now abandoned.

(30) Foreign Application Priority Data

Sep. 30, 2010 (JP) ................................. 2010-223050

(51) Int. Cl.
*G06K 9/00* (2006.01)
*G01N 33/574* (2006.01)
(Continued)

(52) U.S. Cl.
CPC ..... *G06K 9/00134* (2013.01); *G01N 15/1463* (2013.01); *G01N 33/5091* (2013.01);
(Continued)

(58) Field of Classification Search
None
See application file for complete search history.

(56) References Cited

U.S. PATENT DOCUMENTS 6,091,842 A 7/2000 Domanik et al.
6,615,063 B1 * 9/2003 Ntziachristos ....... A61B 5/0073
600/312
(Continued)

FOREIGN PATENT DOCUMENTS

CN 101221118 A 7/2008
JP 10-197522 A 7/1998
(Continued)

OTHER PUBLICATIONS

Office Action, dated Dec. 31, 2013, issued by the State Intellectual Property Office of the People's Republic of China, in counterpart Application No. 201180047721.1.
(Continued)

*Primary Examiner* — Tsung-Yin Tsai
(74) *Attorney, Agent, or Firm* — Sughrue Mion, PLLC

(57) ABSTRACT

The present invention provides an information processing apparatus capable of selecting a region of cancer cells in any tissue sample image and easily and accurately counting the number of the cancer cells. The information processing apparatus is an information processing apparatus 100 including: an acquisition unit 110 for acquiring image data obtained by reading a tissue sample image 150 obtained by putting a mark 151 specifying a selected area 152 on an image obtained by immunostaining and then imaging a biological tissue; and a counting unit 120 for counting the number of cancer cells in the selected area 152 specified by the mark 151 based on the image data of the tissue sample image 150 acquired by the acquisition unit 110, wherein a diagnosis based on the tissue sample image 150 is supported.

7 Claims, 17 Drawing Sheets

(51) Int. Cl.
*G06T 7/00* (2017.01)
*G01N 33/50* (2006.01)
*G01N 15/10* (2006.01)
*G01N 15/14* (2006.01)
*G01N 21/25* (2006.01)

(52) U.S. Cl.
CPC ......... *G01N 33/574* (2013.01); *G06K 9/0014* (2013.01); *G06K 9/00127* (2013.01); *G06T 7/0012* (2013.01); *A61B 2576/00* (2013.01); *G01N 21/251* (2013.01); *G01N 2015/1006* (2013.01); *G01N 2015/1465* (2013.01); *G06K 2209/05* (2013.01); *G06T 2207/10008* (2013.01); *G06T 2207/10024* (2013.01); *G06T 2207/20021* (2013.01); *G06T 2207/20104* (2013.01); *G06T 2207/30024* (2013.01); *G06T 2207/30242* (2013.01)

(56) References Cited

U.S. PATENT DOCUMENTS

| | | | | |
|---|---|---|---|---|
| 6,775,402 | B2* | 8/2004 | Bacus | G01N 15/1475 382/133 |
| 7,146,372 | B2 | 12/2006 | Bacus et al. | |
| 7,177,454 | B2* | 2/2007 | McLaren | G01N 1/312 345/604 |
| 7,558,415 | B2 | 7/2009 | McLaren et al. | |
| 2003/0215936 | A1* | 11/2003 | Kallioniemi | G01N 1/36 435/287.1 |
| 2004/0085443 | A1* | 5/2004 | Kallioniemi | G01N 1/36 348/135 |
| 2007/0135999 | A1* | 6/2007 | Kolatt | G01N 21/31 702/19 |
| 2007/0286468 | A1* | 12/2007 | Joshi | A61B 5/415 382/131 |
| 2010/0054560 | A1* | 3/2010 | Yamashita | A61B 5/055 382/128 |
| 2010/0256496 | A1* | 10/2010 | Zhu | A61B 5/0091 600/459 |
| 2012/0082366 | A1* | 4/2012 | Marugame | G06T 3/00 382/133 |
| 2013/0188857 | A1* | 7/2013 | Yoshihara | G01N 33/574 382/133 |

FOREIGN PATENT DOCUMENTS

| | | |
|---|---|---|
| JP | 2001-510894 A | 8/2001 |
| JP | 2002-42110 A | 2/2002 |
| JP | 2003-066034 A | 3/2003 |
| JP | 2005-502369 A | 1/2005 |
| JP | 3654835 B2 | 6/2005 |
| WO | 99/04243 A1 | 1/1999 |
| WO | 03/023571 A2 | 3/2003 |
| WO | 2008/108059 A1 | 9/2008 |
| WO | 2010/041423 A1 | 4/2010 |

OTHER PUBLICATIONS

Office Action, dated Jul. 1, 2014, issued by the Japanese Patent Office, in counterpart Application No. 2012-536450.

Krajewska, et al., "Image Analysis Algorithms for Immunohistochemical Assessment of Cell Death Events and Fibrosis in Tissue Sections", Journal of Histochemistry & Cytochemistry, vol. 57, No. 7, p. 649-663, 2009.

Communication dated Sep. 11, 2014 from the Japanese Patent Office in counterpart application No. 2012-536450.

* cited by examiner

INFORMATION PROCESSING APPARATUS, INFORMATION PROCESSING SYSTEM, INFORMATION PROCESSING METHOD, PROGRAM, AND RECORDING MEDIUM

This is a divisional application based upon U.S. patent application Ser. No. 13/824,228 filed Mar. 15, 2013, which is a National Stage of International Application No. PCT/JP2011/071931 filed Sep. 27, 2011, claiming priority based on Japanese Patent Application No. 2010-223050 filed Sep. 30, 2010, the contents of all of which are incorporated herein by reference in their entirety.

TECHNICAL FIELD

The present invention relates to an information processing apparatus, an information processing system, an information processing method, a program, and a recording medium.

BACKGROUND ART

In diagnosis based on a tissue sample image of a biological tissue, a region of cancer cells is selected, and the number of the cancer cells is counted. For example, in the patent document 1, information on a tumor region is acquired based on a HE-stained image, and this information is aligned with an IHC-stained image, and thus, a tumor region in the IHC-stained image is specified.

PRIOR ART DOCUMENT

Patent Document

Patent Document 1: WO 2008/108059

SUMMARY OF INVENTION

Problem to be Solved by the Invention

However, it has been really difficult to specify a tumor region in an IHC-stained image, specifically in an image in which cell membranes are barely stained, i.e., the staining is classified as "0". Therefore, it is required that a region of cancer cells in any tissue sample image can be accurately selected, and the number of the cancer cells can be accurately counted.

Hence, the present invention is intended to provide an information processing apparatus, an information processing system, an information processing method, a program, and a recording medium, capable of selecting a region of cancer cells in any tissue sample image and easily and accurately counting the number of the cancer cells.

Means for Solving Problem

In order to achieve the aforementioned object, the information processing apparatus according to the present invention is an information processing apparatus including: an acquisition unit for acquiring image data obtained by reading a tissue sample image obtained by putting a mark specifying a selected area on an image obtained by immunostaining and then imaging a biological tissue; and a counting unit for counting the number of cancer cells in the selected area specified by the mark based on the image data of the tissue sample image acquired by the acquisition unit, wherein a diagnosis based on the tissue sample image is supported.

The information processing system according to the present invention is an information processing system including: the information processing apparatus according to the present invention; an input terminal; and a display terminal, wherein the information processing apparatus includes: a receiving unit for receiving the image data via a network; and a sending unit for sending, via a network, the number of cancer cells counted in the selected area specified by the mark by the counting unit, and the image data received by the receiving unit is input and sent via a network by the input terminal, and the number of cancer cells counted in the selected area specified by the mark by the counting unit is received via a network and displayed by the display terminal.

The information processing method according to the present invention is an information processing method using the information processing apparatus according to the present invention, the method including: an acquiring step of acquiring, by the acquisition unit, image data obtained by reading a tissue sample image with a mark specifying a selected area; and a counting step of counting, by the counting unit, the number of cancer cells in the selected area specified by the mark based on the image data of the tissue sample image acquired by the acquiring step.

The program according to the present invention is a program capable of executing the information processing method according to the present invention on a computer.

The recording medium according to the present invention is a computer-readable recording medium including: the program according to the present invention.

Effects of the Invention

According to the present invention, a region of cancer cells in any tissue sample image can be selected, and the number of the cancer cells can be counted easily and accurately.

DESCRIPTION OF EMBODIMENTS

Embodiments of the present invention are illustrated in detail below with reference to figures. Components described in the following embodiments, however, are mere examples, and the technical scope of the present invention is not limited only thereby.

First Embodiment

Figure 1:
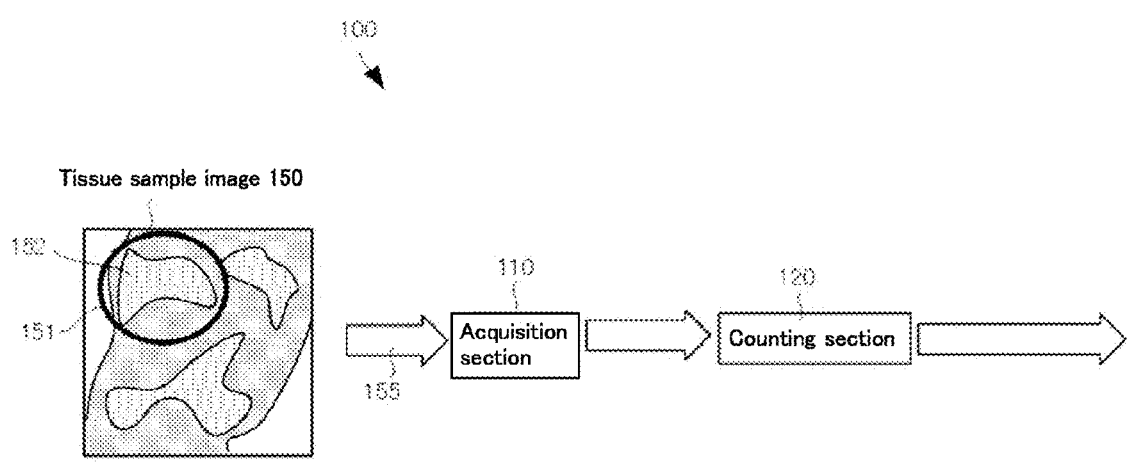
FIG. 1 is a block diagram showing a configuration of an information processing apparatus according to the first embodiment of the present invention.

An information processing apparatus 100 according to the first embodiment of the present invention is described with reference to FIG. 1. FIG. 1 shows the information processing apparatus 100 which supports a diagnosis based on a tissue sample image 150 obtained by immunostaining and then imaging a biological tissue. The information processing apparatus 100 includes: an acquisition section (acquisition unit) 110 for acquiring image data 155 obtained by reading the tissue sample image 150 with a mark 151 put thereon and specifying a selected area 152. The information processing apparatus 100 further includes: a counting section (counting unit) 120 for counting the number of cancer cells in the selected area specified by the mark 151 based on the image data 155 of the tissue sample image 150 acquired by the acquisition section 110. With the above-described configuration, a region of cancer cells in any tissue sample image can be easily and accurately selected, and the number of the cancer cells can be easily and accurately counted. It is to be noted that the "selected area" is also referred to as a "focus area" in the present invention.

Second Embodiment

<Configuration of Information Processing System Including Pathological Image Diagnosis Support Apparatus as Information Processing Apparatus According to the Second Embodiment>

Figure 2:
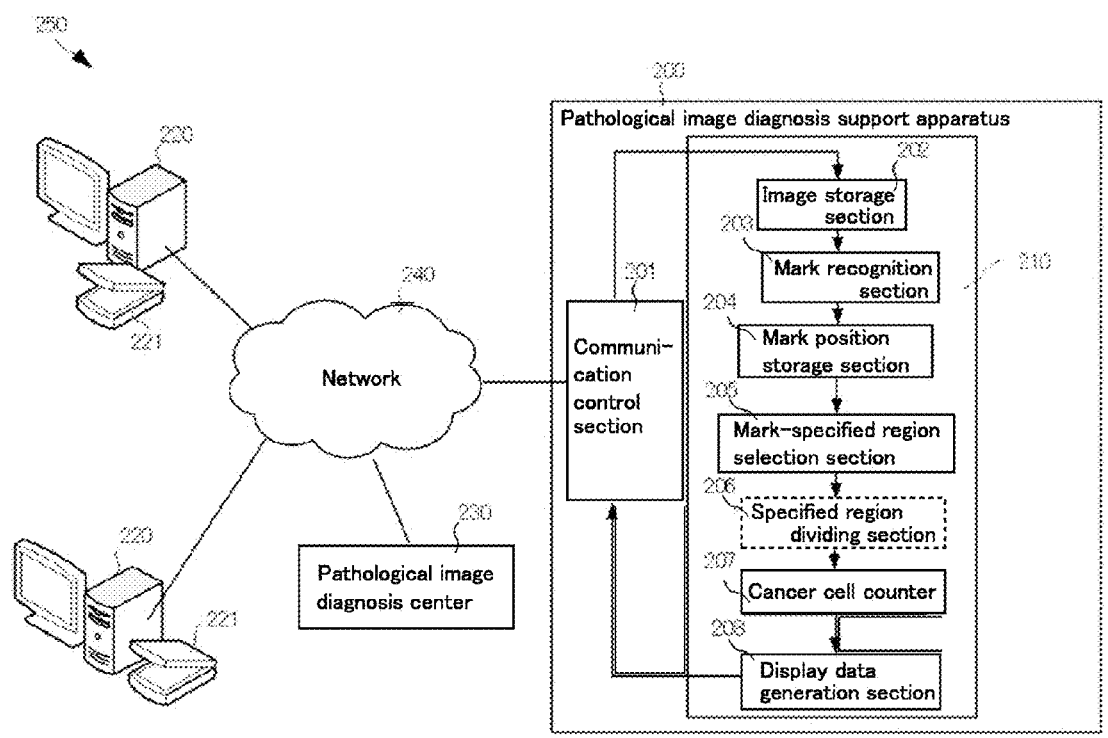
FIG. 2 is a block diagram showing a configuration of an information processing system according to the second embodiment of the present invention.

FIG. 2 is a block diagram showing a configuration of an information processing system 250 including a pathological image diagnosis support apparatus 200 as the information processing apparatus according to the second embodiment. In FIG. 2, the pathological image diagnosis support apparatus 200 is connected, via a network 240, to a plurality of client PCs 220 each of which includes a color scanner 221 for reading (inputting) a tissue sample image thereinto. The pathological image diagnosis support apparatus 200 is also connected to a pathological image diagnosis center 230 for sending an image or results obtained through processes by the pathological image diagnosis support apparatus 200 so that specialized physicians can analyze and diagnose. The pathological image diagnosis support apparatus 200 corresponds to the information processing apparatus according to the present invention. It can be said that each of the client PCs 220 and the color scanners 221 corresponds to an "input terminal" of the information processing system according to the present invention. It can be said that each of the client PCs 220 also corresponds to a "display terminal" of the information processing system according to the present invention. It can be said that the pathological image diagnosis center 230 also corresponds to a "display terminal" of the information processing system according to the present invention. The network 240 may be a public network including the Internet or an in-hospital LAN.

The communication control section 201 of the pathological image diagnosis support apparatus 200 receives a tissue sample image with a mark sent from a client PC 220 via a network (i.e., image data obtained by reading the tissue sample image with a mark by a color scanner 221). That is, it can be said that the communication control section 201 corresponds to a "receiving unit" for receiving, via a network 240, the tissue sample image with a mark. The received tissue sample image with a mark (image data) is stored in an image storage section (image storage unit) 202. It can be said that the image storage section (image storage unit) 202 corresponds to an "acquisition unit" for acquiring image data obtained by reading the tissue sample image with a mark. In a mark recognition section (mark recognition unit) 203, a mark on the tissue sample image with the mark is recognized together with the position thereof. In a mark position storage section (mark position storage unit) 204, the position of the recognized mark is stored. This storage allows superimposing a tissue sample image in the fourth embodiment described below. In a mark-specified region selection section (a selection unit or a mark-specified region selection unit) 205, a mark-specified region is selected based on the tissue sample image with the mark and the position of the mark stored in the image storage section 202. In the present embodiment, the inside of the mark which is a closed curve is a specified region. The present invention, however, is not limited thereto, and a region including the position of the mark may be automatically set as a mark-specified region. A mark is not limited to only one, and there may be a plurality of marks. In a specified region dividing section (a dividing unit or a specified region dividing unit) 206, a mark-specified region of the third embodiment described below is divided into meshes, and the divided regions are transmitted to a cancer cell counter (counting unit) 207.

The cancer cell counter 207 counts the number of cancer cells with each staining intensity in a parenchymal cell region to be observed in the mark. In a display data generation section (display data generation unit) 208, send data is generated based on a count value obtained by counting the number of cancer cells with each staining intensity by the cancer cell counter 207, the tissue sample image, or the mark. Desired display data in a diagnosable format is selected as the display data by the client PC 220. The selected display data is sent from the communication control section 201 to the client PC 220 via the network and is displayed on a display screen. Alternatively, the selected display data is sent to the pathological image diagnosis center 230 so that specialized physicians can analyze and diagnose. That is, it can be said that the communication control section 201 also corresponds to a "sending unit" for sending, via a network 240, a count value obtained by counting the number of cancer cells in the selected area specified by the mark of the tissue sample image by the counting unit.

<Processing Sequence in Information Processing System According to the Second Embodiment>

A processing sequence in the information processing system according to the second embodiment is shown below with reference to FIG. 3.

In a sequence S301, a color scanner 221 reads a slide with a mark which is a tissue sample image with a mark. In a sequence S303, the read tissue sample image with a mark is then sent from the color scanner 221 to a client PC 220 and is sent to a pathological image diagnosis support apparatus 200 which is the information processing apparatus. That is, it can be said that a series of the sequences S301 and S303 corresponds to an "inputting and sending step" of, by the input terminal, inputting (reading) and sending, via a network, image data received by a receiving unit (communication control section 201). In a sequence S305, the pathological image diagnosis support apparatus 200 receives the image data from a communication control section 201 (receiving step), then acquires the image data in an image storage section (acquisition unit) 202 (acquiring step), and recognizes the mark in the mark recognition section 203. The mark is a mark put on the slide of the tissue sample image by a physician with a magic marker in order to separate a focus area of stained positive cells (an area in which the number of cancer cells is counted) from the other area, for example.

Figure 3:
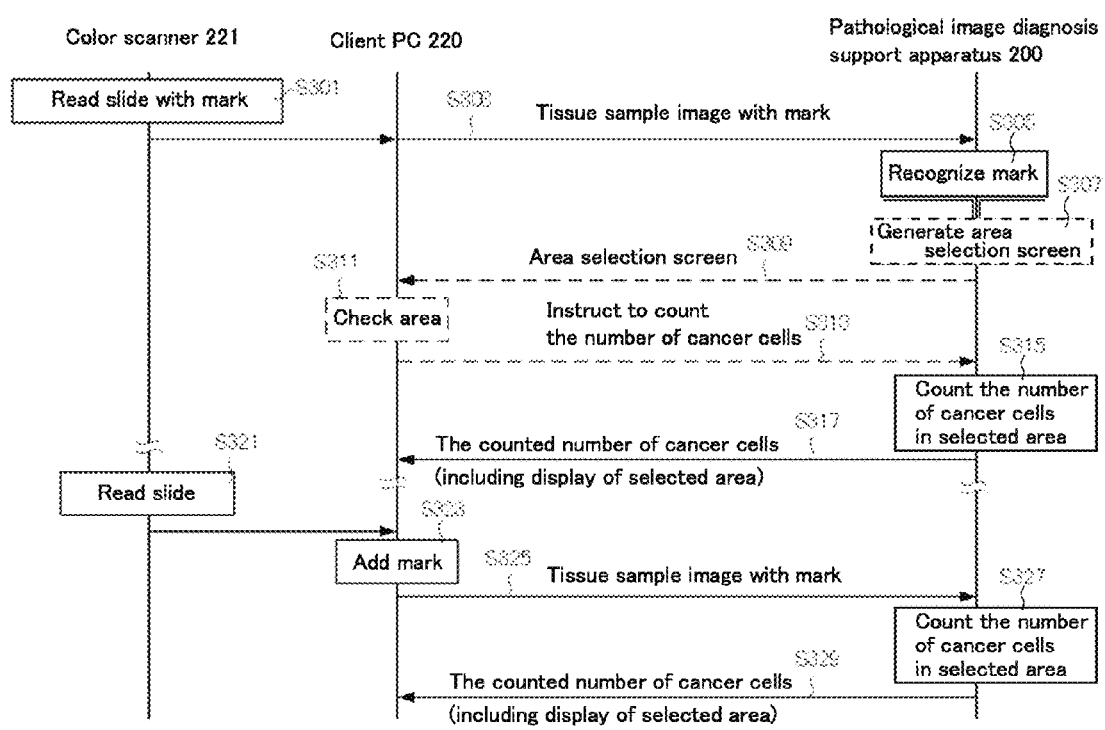
FIG. 3 is a sequence diagram showing a processing sequence in the information processing system according to the second embodiment of the present invention.

In sequences S307 to S313 indicated by a dotted line in FIG. 3, a result of the mark recognition is displayed on the client PC 220, and the selected area in the mark is checked. These sequences, however, are performed optionally. For example, when the mark is not closed as a closed curve, it becomes necessary for a user to check an area in which the number of cancer cells is counted. A mark other than this may be a point indicating the center position of the area or a line segment indicating a part of the edge of the area. First, in the sequence S307, a screen for selecting an area (hereinafter referred to as an "area selection screen") (see FIG. 8 described below) is generated. In the sequence S309, the generated area selection screen is then sent from the pathological image diagnosis support apparatus 200 to the client PC 220. In the sequence S311, the area selection screen is displayed on the client PC 220, and the area is checked. Subsequently, in the sequence S313, an instruction of counting the number of cancer cells in the area by a user is sent to the pathological image diagnosis support apparatus 200.

In a sequence S315 (counting step), the pathological image diagnosis support apparatus 200 counts the number of cancer cells in the selected area in the mark. If a checking sequence, i.e., a series of the sequences S307 to S313 indicated by a dotted line is not performed, the sequence is shifted from the sequence S305 to the sequence S315. In a sequence S317 (sending step), the counted number of cancer cells is sent. The sending of the counted number of cancer cells includes sending of display data of the selected area.

(Variation of Processing Sequence)

A series of sequences S321 to S329 of FIG. 3 is a variation of the processing sequence. In the sequence S321, a slide with or without a mark is read as a tissue sample image. In the sequence S323, a mark is added on a display screen of the acquired tissue sample image by the client PC 220 (see FIG. 7 described below). In the sequence S325, the tissue sample image with the added mark or the tissue sample image with the mark which has been put thereon and the added mark is sent from the client PC 220 to the pathological image diagnosis support apparatus 200. In the sequence S327, the pathological image diagnosis support apparatus 200 counts the number of cancer cells in each selected area in the put mark and/or the added mark. In the sequence S329, the counted number of cancer cells is sent. The sending of the counted number of cancer cells includes sending of display data of the selected area.

<Hardware Configuration of Pathological Image Diagnosis Support Apparatus>

Figure 4A:
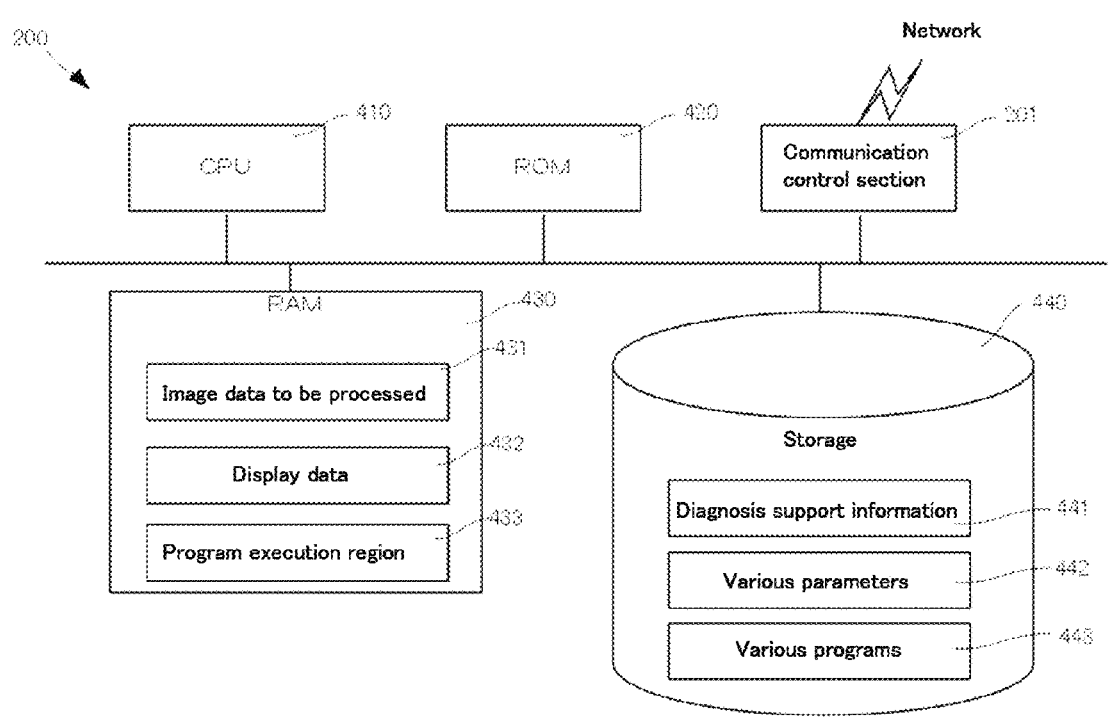
FIG. 4A is a block diagram showing a hardware configuration of a pathological image diagnosis support apparatus according to the second embodiment of the present invention.

FIG. 4A is a block diagram showing a hardware configuration of the pathological image diagnosis support apparatus 200 as an information processing apparatus according to the second embodiment. As shown in FIG. 4A, the pathological image diagnosis support apparatus 200 includes: a CPU (Central Processing Unit) 410; a ROM (Read Only Memory) 420; a communication control section 201; a RAM (Random Access Memory) 430; and a storage 440.

In FIG. 4A, the CPU 410 is an arithmetic and control processor and executes programs so that functions of sections of FIGS. 2 and 3 can be achieved. The ROM 420 stores fixed data such as initial data and initial programs and programs. As described for FIG. 2, the communication control section 201 communicates, via the network 240, with client PCs 220 and the pathological image diagnosis center 230 which are outside devices.

The RAM 430 is a temporal storage section used as a working area for temporal storage by the CPU 410. Generally, image data to be processed 431 and display data 432 are temporally stored in the RAM 430. The RAM 430 includes a program execution region 433 for executing programs by the CPU 410.

The storage 440 is a nonvolatile storage of diagnosis support information 441, various parameters 442, and various programs 443.

Figure 4B:
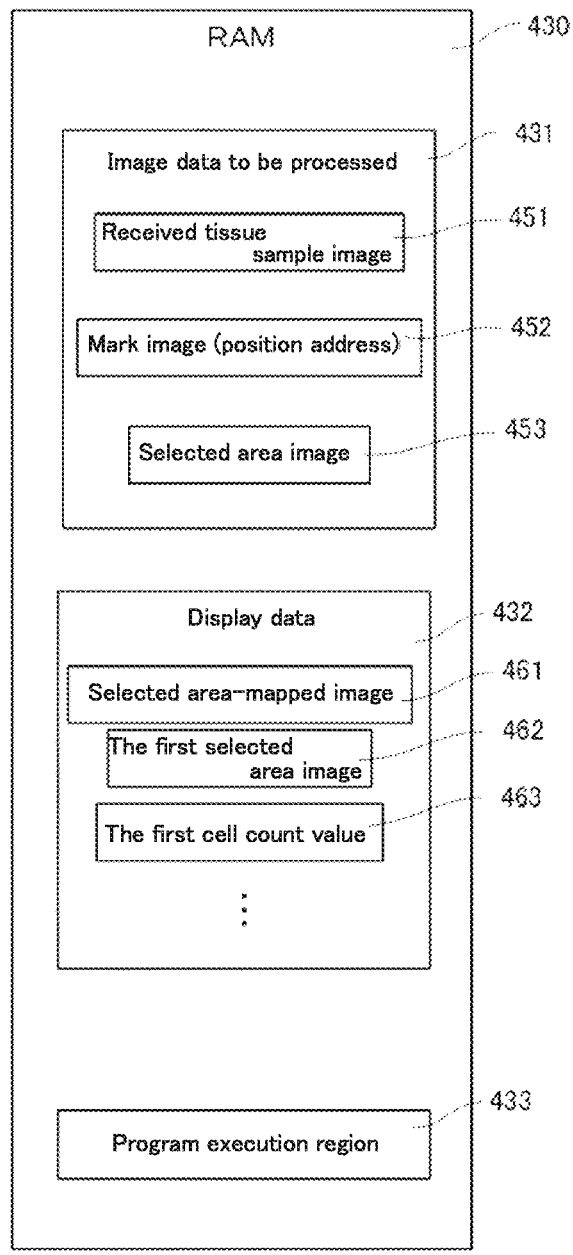
FIG. 4B is a block diagram showing a configuration of a RAM in the pathological image diagnosis support apparatus according to the second embodiment of the present invention.

As shown in FIG. 4B, the image data 431 to be processed in the RAM 430 includes the following data.
  a tissue sample image with a mark 451 received via the communication control section 201
  a mark image 452 recognized from the tissue sample image with a mark
Storage of the mark image may be storage of an address of the position of the mark image or a closed curve generated based on thinning, smoothing, or the mark image.
  an image 453 of one selected area selected from the received tissue sample image The display data 432 sent to the client PC 220 via the communication control section 201 includes the following data.
  a selected area-mapped image 461 obtained by mapping the selected area into the received tissue sample image
  the first selected area image 462 of the first selected area
  the first cell count value 463 which is the counted number of cancer cells with each staining intensity in the first selected area image The same kind of data is included in display data 432 for each of subsequent selected areas.

Figure 4C:
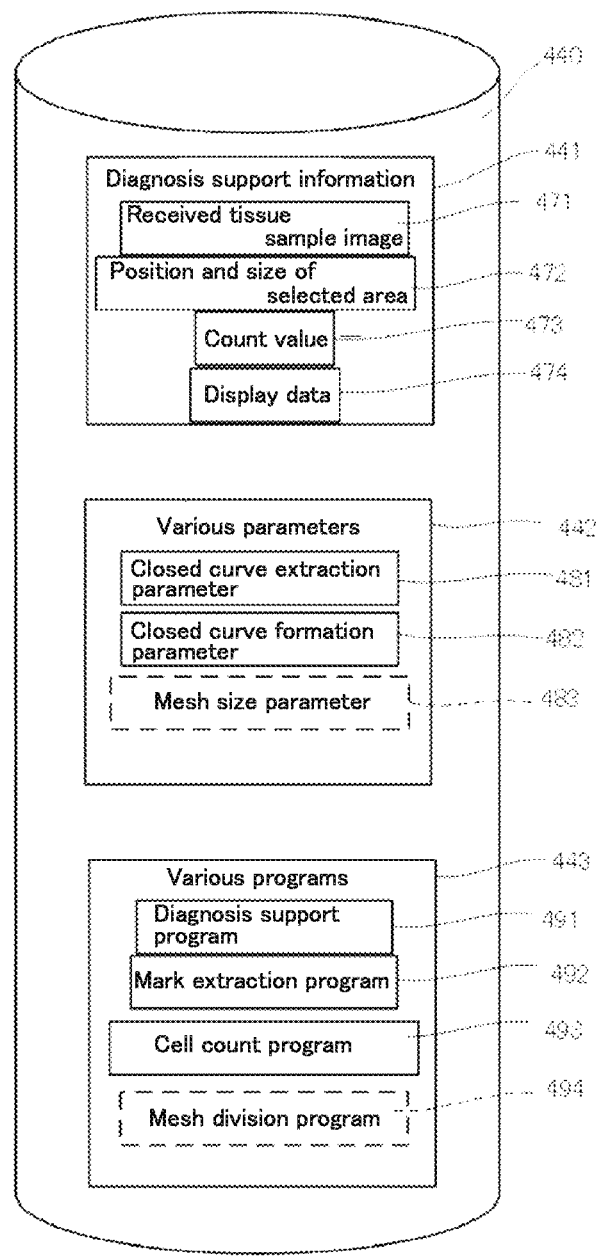
FIG. 4C is a block diagram showing a configuration of a storage in the pathological image diagnosis support apparatus according to the second embodiment of the present invention.
Figure 5:
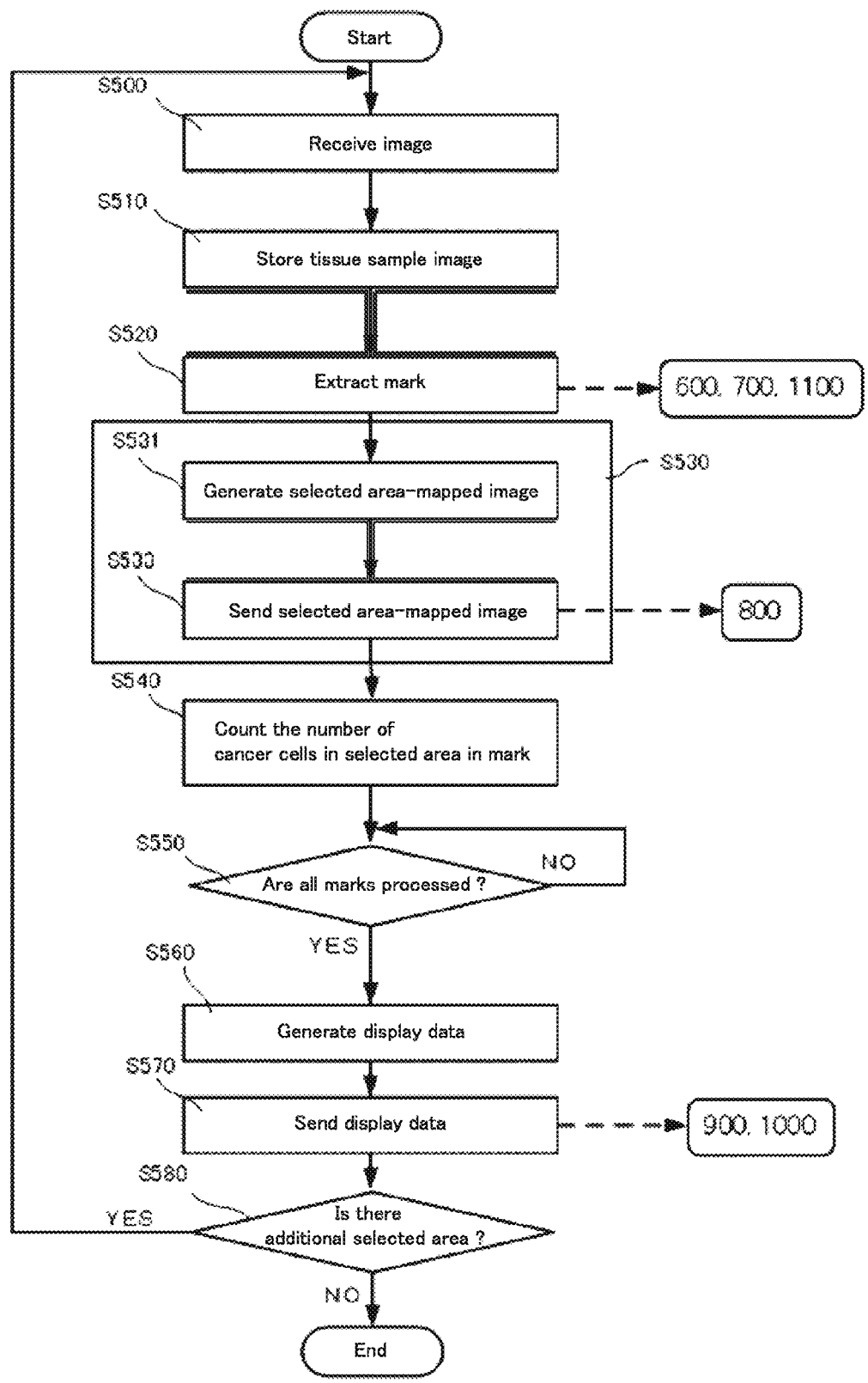
FIG. 5 is a flowchart showing a procedure for operating the pathological image diagnosis support apparatus according to the second embodiment of the present invention.

As shown in FIG. 4C, the diagnosis support information 441 in the storage 440 includes the following data.
  a received tissue sample image 471 the position and size 472 of the selected area as a partial region selected from the tissue sample image the count value 473 relating to cancer cells in the selected area processed display data 474 stored so as to be searchable by the tissue sample image, the patient, the case, and the like As shown in FIG. 4C, various parameters 442 in the storage 440 include the following parameters.

a closed curve extraction parameter 481 for extracting the put mark or the added mark on the tissue sample image For example, when a color of each mark is previously set so as to be distinguishable on a tissue sample image, the closed curve extraction parameter 481 is used as a parameter indicating the color. When the shape of each mark is previously set to circle, rectangle, or the like so as to be distinguishable on a tissue sample image, the closed curve extraction parameter 481 is used as a parameter indicating the shape.

a closed curve formation parameter 482 for distinguishing and complementing a non-closed line so as to be a closed curve when the mark put by a user is a simple circular non-closed curve As shown in FIG. 4C, various programs 443 in the storage 440 include the following programs.

a diagnosis support program 491 for supporting diagnosis a mark extraction program 492 for extracting a mark on a tissue sample image and recognizing a selected area (for executing S520 of FIG. 5)

a cell count program 493 for counting the number of cells with each staining intensity in the image of the selected area (for executing S540 of FIG. 5)

<Procedure for Operating Pathological Image Diagnosis Support Apparatus 200 According to the Second Embodiment>

A procedure for operating a pathological image diagnosis support apparatus 200 having the above-described configuration is described in detail below with reference to flowcharts and examples of display screens. A CPU 410 executes programs shown in each flowchart so that functions of the components in FIG. 2 are achieved.

(Procedure for Supporting Diagnosis)

FIG. 5 is a flowchart showing an overall procedure for supporting diagnosis in the present embodiment.

Figure 6:
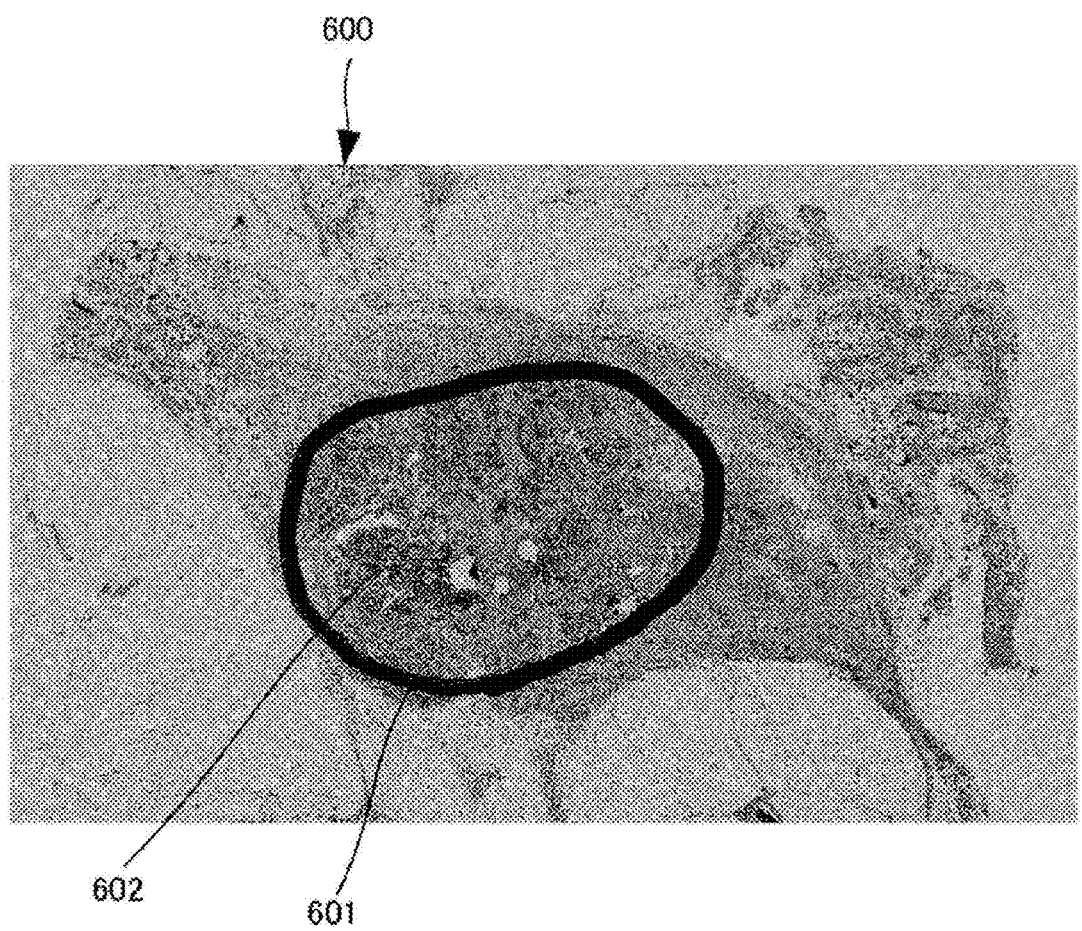
FIG. 6 is a figure showing the first example of a tissue sample image with a mark according to the second embodiment of the present invention.
Figure 7:
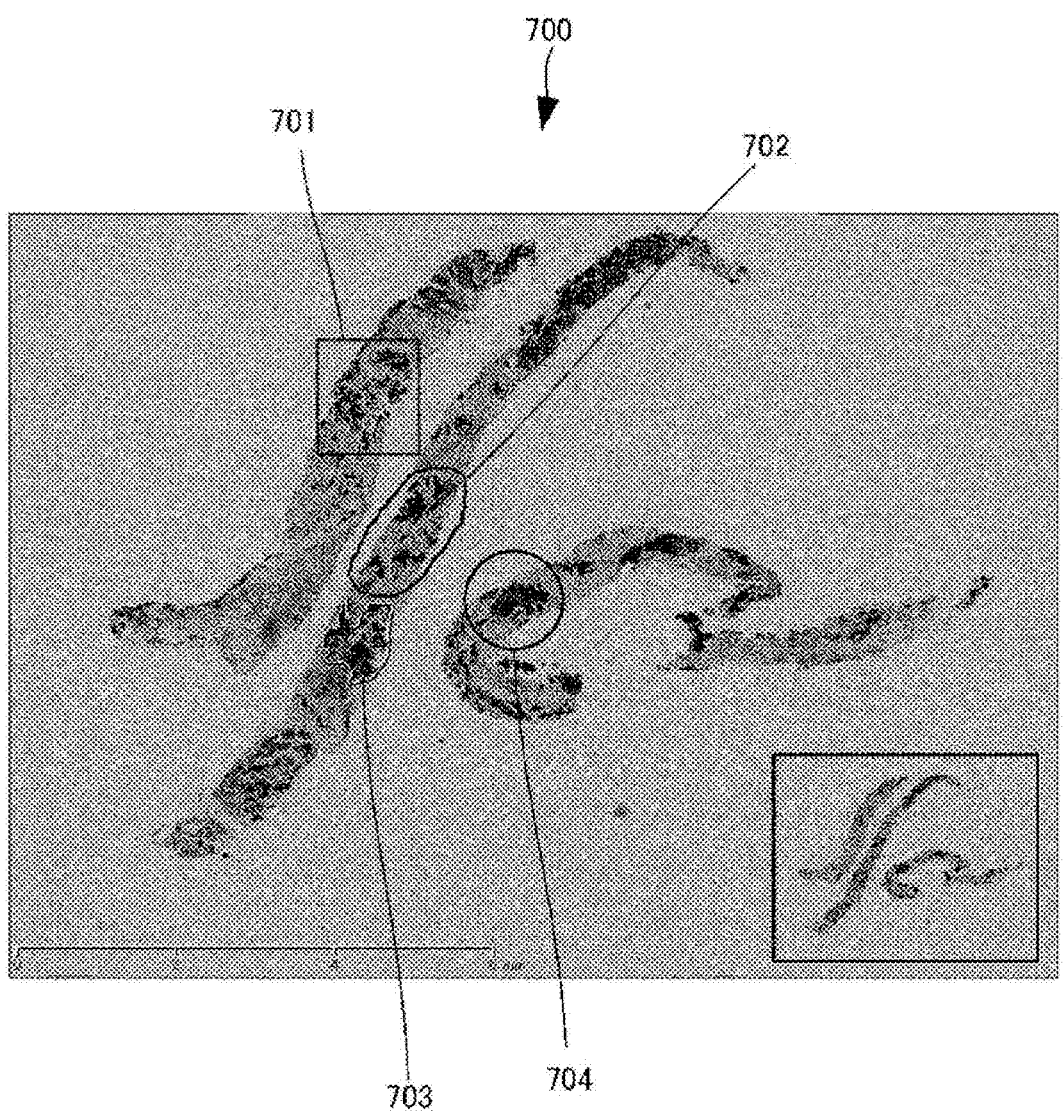
FIG. 7 is a figure showing the second example of a tissue sample image with marks according to the second embodiment of the present invention.

In a step S500 (receiving step), the pathological image diagnosis support apparatus 200 waits for a tissue sample image with a mark to be sent from a client PC 220. When the tissue sample image with a mark is received, it is stored in a step S510 (acquiring step). FIG. 6 shows the first example of the tissue sample image with a mark, and FIG. 7 shows the second example of the tissue sample image with marks. In the tissue sample image 600 with a mark of FIG. 6, a mark 601 which is a closed curve enclosing a region 602 in which a user desires to count the number of cancer cells is drawn in, for example, dark blue although it is not distinguished in FIG. 6. In the tissue sample image 700 with marks of FIG. 7, a rectangular mark 701 and marks 702 to 704 which are closed curves, enclosing each region in which a user desires to count the number of cancer cells are drawn in the respective colors although it is not distinguished in FIG. 7, for example. The difference between FIGS. 6 and 7 is as follows. In FIG. 6, the mark is drawn on a slide by a user with a magic marker or the like. In FIG. 7, the marks are overlaid on the display screen of the client PC 220. The mark drawn on a slide and the mark overlaid on the display screen may be present together.

In a step S520, a mark is extracted from the received tissue sample image with the mark, and a selected area is recognized. Various methods are known as a method for extracting a mark or a method for recognizing a selected area, and any of them can be used.

Figure 8:
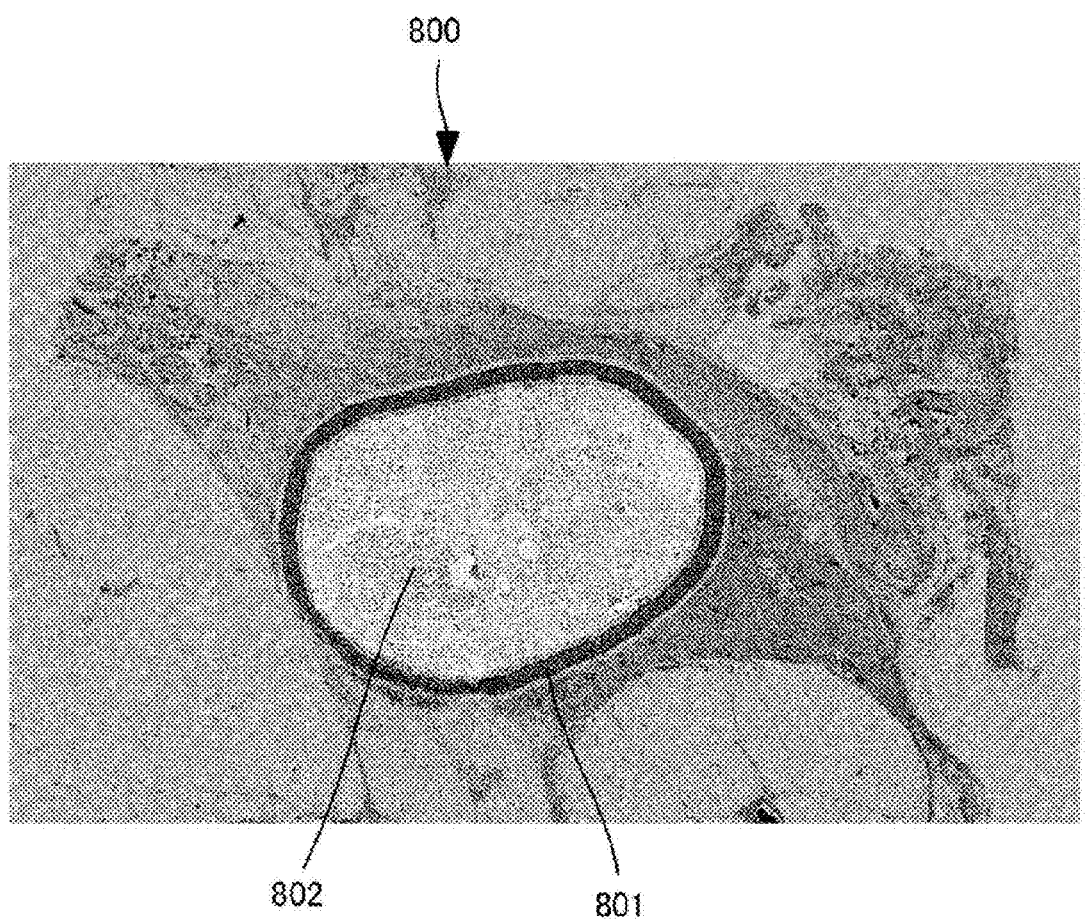
FIG. 8 is a figure showing an image for checking a selected area according to the second embodiment of the present invention.

A step S530 is a step of checking a selected area with a user, corresponding to a series of sequences S307 to S313. First, in a step S531, an image is generated by mapping a selected area into the tissue sample image. In a step S533, the selected area-mapped image thus obtained is sent to the client PC 220. FIG. 8 shows an example of a display of the selected area-mapped image. In a selected area-mapped image 800 of FIG. 8, a closed curve 801 extracted from a mark is displayed in pink, and a selected area 802 is filled in green. Thus, the display is converted into a display easily checked by a user. Then, the pathological image diagnosis support apparatus 200 waits for a user to check and accept, and when it is instructed to count the number of cancer cells, the step is shifted to a step S540.

Figure 9:
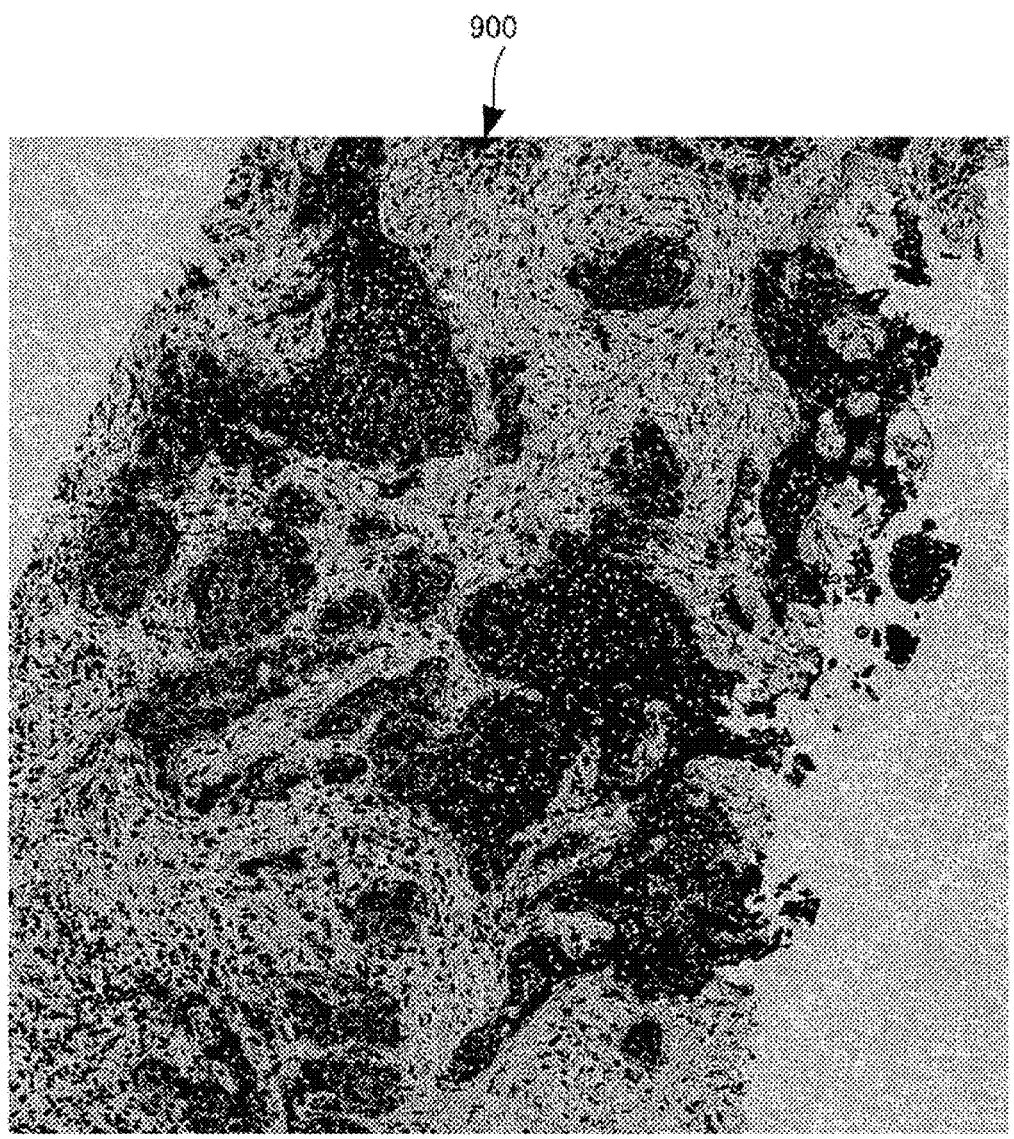
FIG. 9 is a figure showing the first example of a send image according to the second embodiment of the present invention.
Figure 10:
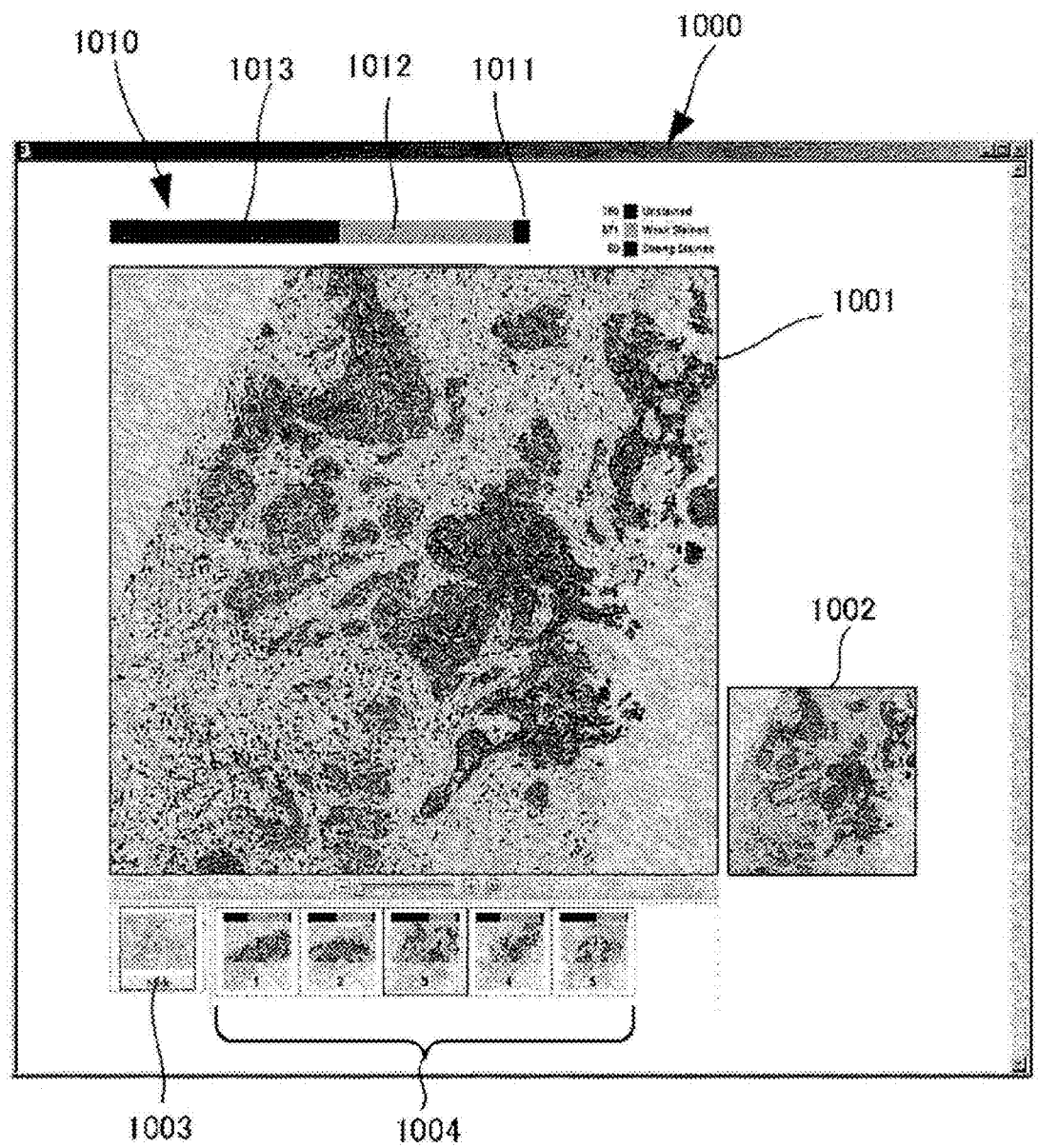
FIG. 10 is a figure showing the second example of a send image according to the second embodiment of the present invention.

In the step S540 (counting step), the number of the cancer cells with each staining intensity in the selected area in the mark is counted. In the case of including a plurality of marks, the pathological image diagnosis support apparatus 200 waits for all of selected areas indicated by the marks to be processed completely in a step S550. When all of the selected areas are processed completely, the step is shifted to a step S560. In the step S560, display data of the counted number of cancer cells is generated in order to send it to the client PC 220. FIG. 9 shows the first example of a display screen displaying the counted number. FIG. 10 shows the second example of a display screen displaying the counted number. The display screen of FIG. 9 includes a tissue sample image 900 of the selected area and the counted number 901 with each staining intensity. In the tissue sample image 900, cells with each staining intensity are colored a different color and then displayed, and the description thereof, however, is omitted. A display screen 1000 of FIG. 10 includes: an enlarged tissue sample image 1001 of one selected area; a reduced-size image 1002 of the selected area; and a thumbnail image 1003 of the tissue sample image. The display screen 1000 further includes: thumbnail images 1004 of five selected areas, each including a bar-graph; and a bar-graph 1010 according to the selected area. The bar-graph 1010 includes: a region 1011 indicating the number of cells with "strong" staining intensity, a region 1012 indicating the number of cells with "weak" staining intensity, and a region 1013 indicating the number of cells with "none" of staining intensity, for example. The thumbnail image 1003 of the entire tissue sample image and the thumbnail images 1004 of five selected area, each including a bar-graph are displayed as buttons. FIG. 10 shows the case where the third selected area indicated by the numeral "3" is selected. A dark box of the third selected area indicated by the numeral "3" among the thumbnail images of the five selected areas indicates the result that the third selected area is selected. In a step S507 (sending step), the generated display data is sent to the client PC 220.

(Example of Adding Selected Area)

Figure 11:
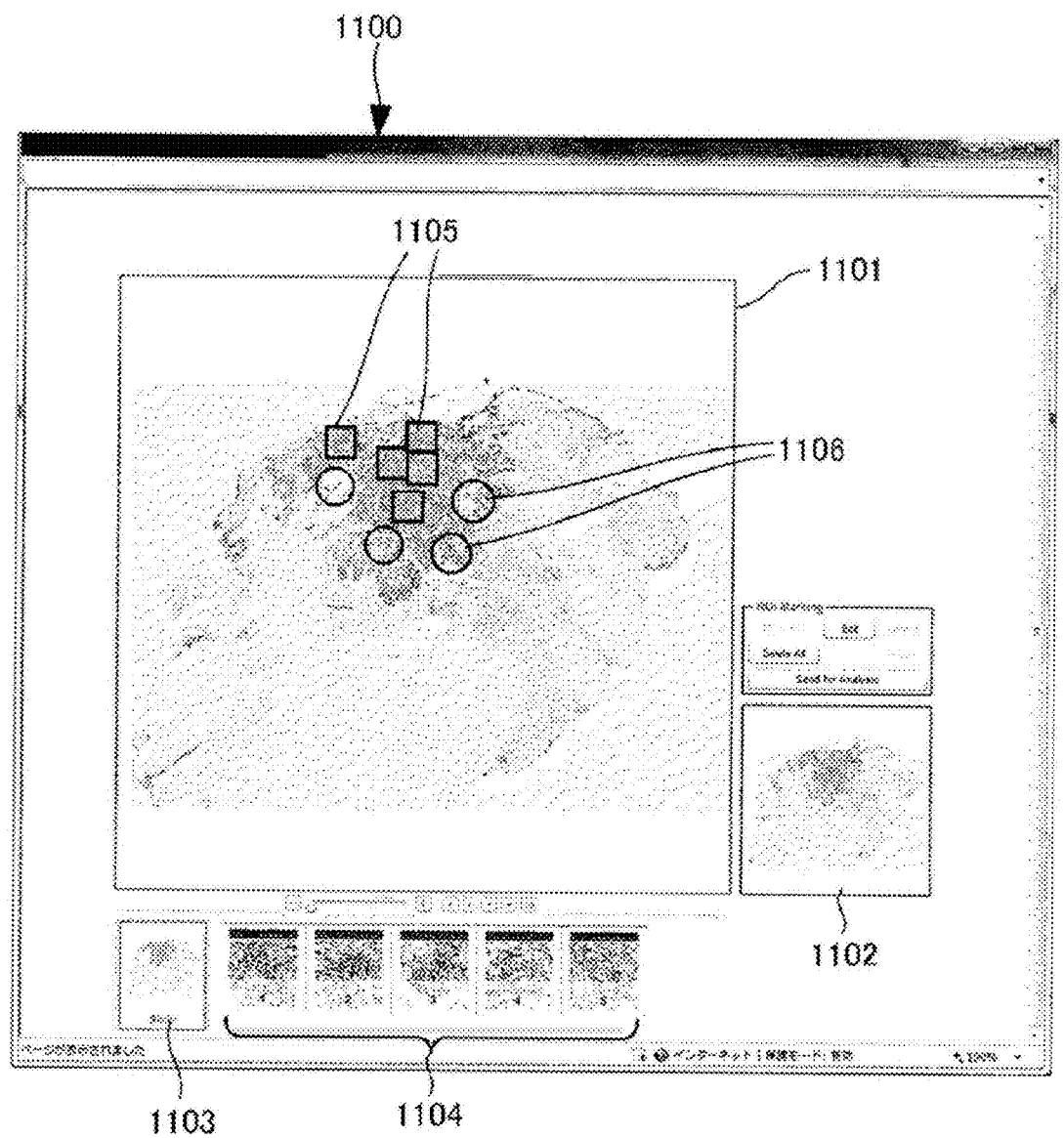
FIG. 11 is a figure showing the third example of a tissue sample image with marks according to the second embodiment of the present invention.

In a step S580, whether or not a user added a selected area and instructed to count the number of cells is determined from the result displayed on the client PC 220. When it is determined that a user added a selected area, the pathological image diagnosis support apparatus 200 waits for a tissue sample image with a mark specifying the added selected area to be sent in the step S500. When the tissue sample image is received, the steps from S510 to S570 are performed. FIG. 11 shows a tissue sample image with marks specifying added selected areas. In a display image 1100 of FIG. 11, marks 1106 of the added selected areas are superimposed on a tissue sample image 1101 in addition to marks 1105 of selected areas in each of which the number of cells has been counted. Although not shown in FIG. 11, the marks 1105 are indicated by red, and the marks 1106 are indicated by yellow, so that they are distinguishable, for example. The numerals 1102 to 1104 indicate thumbnail images of selected areas in each of which the number of cells has been counted as buttons for selection as indicated by the numerals 1002 to 1004 of FIG. 10.

Third Embodiment

The third embodiment shows an example of dividing a selected area into meshes and counting the number of cells in each small area of each mesh when the large number of cancer cells is contained or masses of cancer cells are spread in the selected area in a mark, for example. Alternatively, a selected area may be divided into meshes, the number of cells in each mesh may be counted, and the total number of cells may be used as the counted number. In this case, even if a part of the selected area in a mark has a score of +3, wrong diagnosis might be made by using the average of scores as a determination result. Therefore, the following is desired. Some meshes are automatically selected from the meshes into which a selected area is divided, and scores in the selected meshes are determined, or meshes are superimposed on a selected area, and a user is requested to select meshes for determining scores thereof. In the present embodiment, as shown in FIG. 4C, the storage 440 includes a mesh size parameter 483 as one of various parameter 442. The mesh size parameter 483 is used as a parameter for dividing a selected area into meshes when the large number of cancer cells is contained or masses of cancer cells are spread in the selected area in a mark, for example (see FIG. 13). The storage 440 further includes a mesh division program 494 as one of various programs 443. This program is used to divide a selected area into meshes and executes S1201 of FIG. 12.

<Processing Sequence in Information Processing System According to the Third Embodiment>

Figure 12:
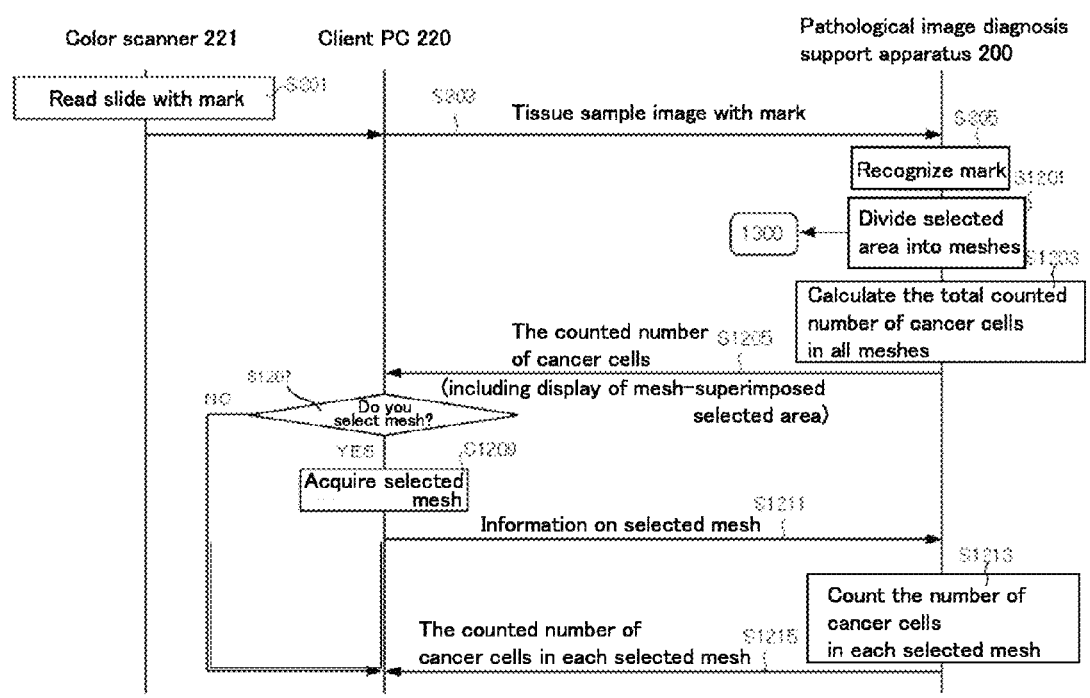
FIG. 12 is a sequence diagram showing a processing sequence in an information processing system according to the third embodiment of the present invention.

A processing sequence in the information processing system according to the third embodiment is shown below with reference to FIG. 12.

In a sequence S301, a color scanner 221 reads a slide with a mark which is a tissue sample image with a mark. In a sequence S303, the read tissue sample image with a mark is then sent from the color scanner 221 to a client PC 220 and is sent to a pathological image diagnosis support apparatus 200 which is an information processing apparatus. In a sequence S305, the pathological image diagnosis support apparatus 200 recognizes the mark. The above-described sequences are the same as those in FIG. 3 of the second embodiment.

Figure 13:
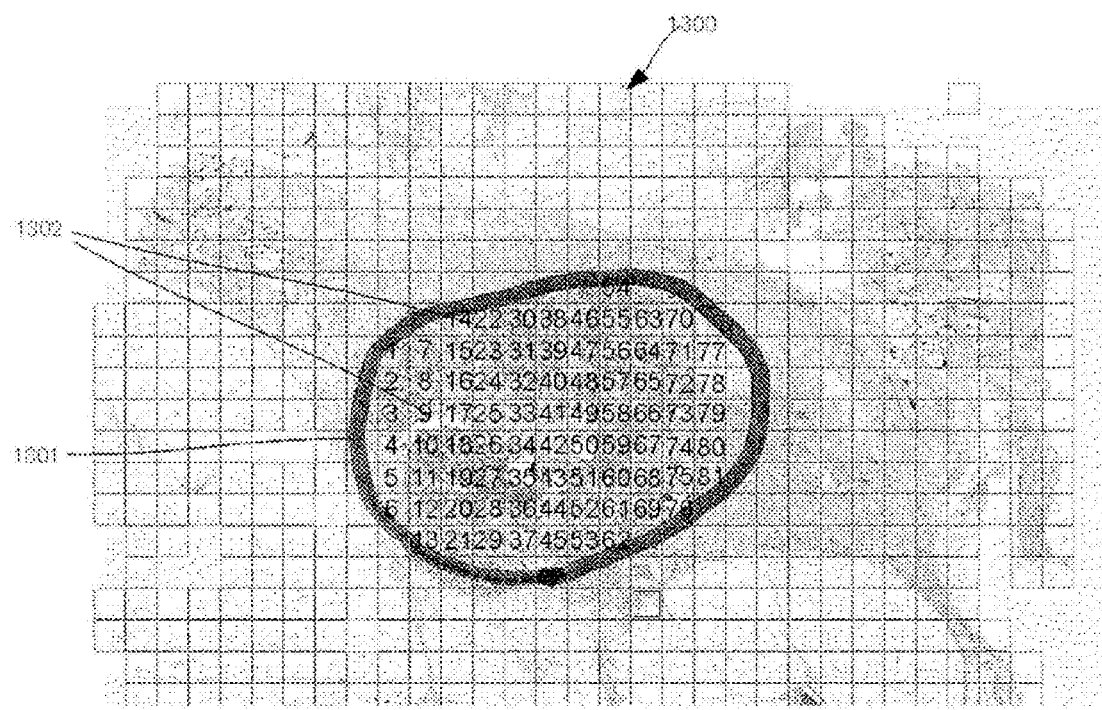
FIG. 13 is a figure showing a selected area divided into meshes in the third embodiment of the present invention.

Subsequently, in a sequence S1201, the pathological image diagnosis support apparatus 200 divides the selected area selected with the mark into meshes. The selected area is divided using the mesh size parameter 483 shown in FIG. 4C. The mesh size is appropriately set according to the size, the enlargement ratio, the resolution, the number of cells in one mesh, and the like, for example. FIG. 13 shows an example of a display obtained by dividing a selected area selected with a mark into meshes. In a display image 1300 of FIG. 13, the selected area in a mark 1301 is divided into 81 mesh regions 1302. In a sequence S1203, the number of cells in each mesh is counted, and the total counted number of cells in the 81 mesh regions 1302 is calculated by the pathological image diagnosis support apparatus 200. Then, in a sequence S1205, the total counted number of cancer cells is sent to the client PC 220 as a result of the total counted number of cancer cells. It is desired that the send data includes display data of the selected area with meshes superimposed thereon of FIG. 13.

In a sequence S1207, whether or not a user instructed to count the number of cells not in the entire selected area but in each of the selected meshes is determined from the selected area with meshes superimposed thereon, displayed on the client PC 220. When no instruction of selecting meshes (hereinafter referred to as a "selection instruction") was made, a process is terminated. When a selection instruction was made, meshes specified according to the selection instruction are acquired in a sequence S1209. The client PC 220 sends information (the mesh number or mesh position information) on the meshes selected in a sequence S1211 to the pathological image diagnosis support apparatus 200. The pathological image diagnosis support apparatus 200 counts the number of cells in each selected mesh in a sequence S1213 and sends the counted number of cancer cells in each selected mesh in a sequence S1215 to the client PC 220.

Fourth Embodiment

In the fourth embodiment, a plurality of tissue sample images obtained through staining by a plurality of staining methods shares a mark extracted from one tissue sample image with the mark. In the present embodiment, a mark extracted from a HE-stained slide with the mark is applied to an IHC-stained slide without the mark, and then the number of cancer cells in the mark is counted.

<Processing Sequence in Information Processing System According to the Fourth Embodiment>

Figure 14:
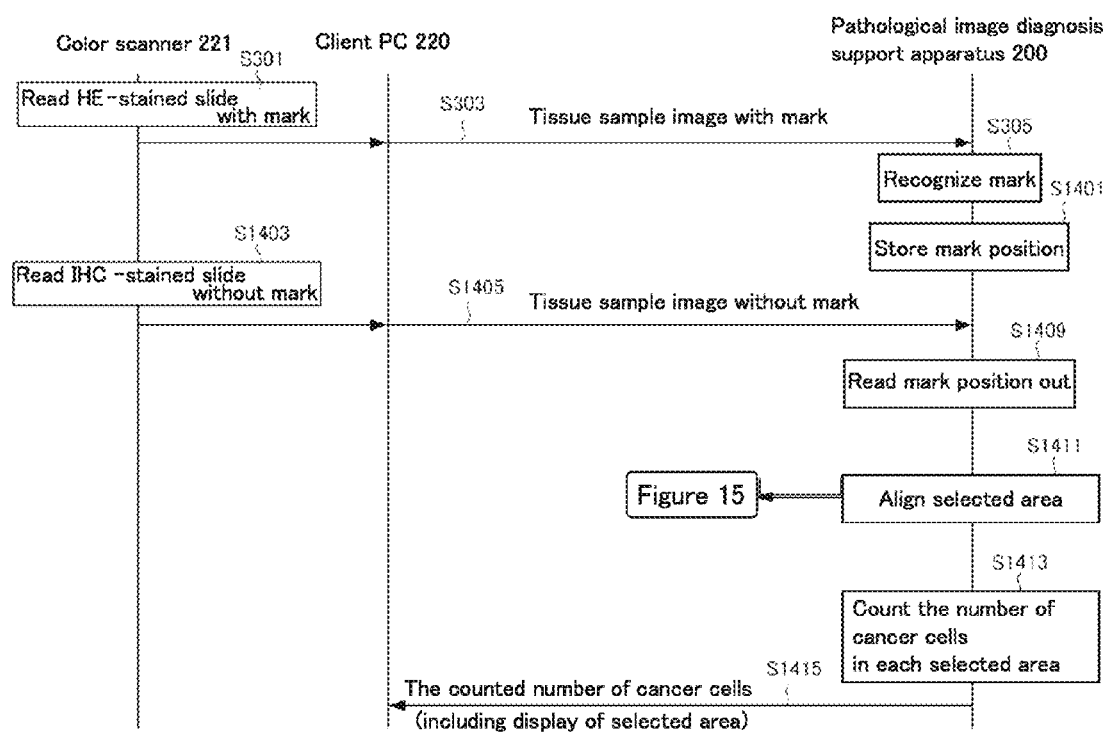
FIG. 14 is a sequence diagram showing a processing sequence in an information processing system according to the fourth embodiment of the present invention.

FIG. 14 is a figure showing a processing sequence in the information processing system according to the fourth embodiment. In a sequence S301, a color scanner 221 reads a HE-stained slide with a mark which is a tissue sample image with a mark. In a sequence S303, the read tissue sample image with a mark is then sent from the color scanner 221 to a client PC 220 and is further sent to a pathological image diagnosis support apparatus 200. In a sequence S305, the pathological image diagnosis support apparatus 200 recognizes the mark. Subsequently, in a sequence S1401 (mark position storing step), the pathological image diagnosis support apparatus 200 stores a position of the mark.

On the other hand, in a sequence S1403, the color scanner 221 reads an IHC-stained slide without the mark which is a tissue sample image without the mark. In a sequence S1405, the read tissue sample image without the mark is then sent from the color scanner 221 to the client PC 220 and is further sent to the pathological image diagnosis support apparatus 200.

Figure 15:
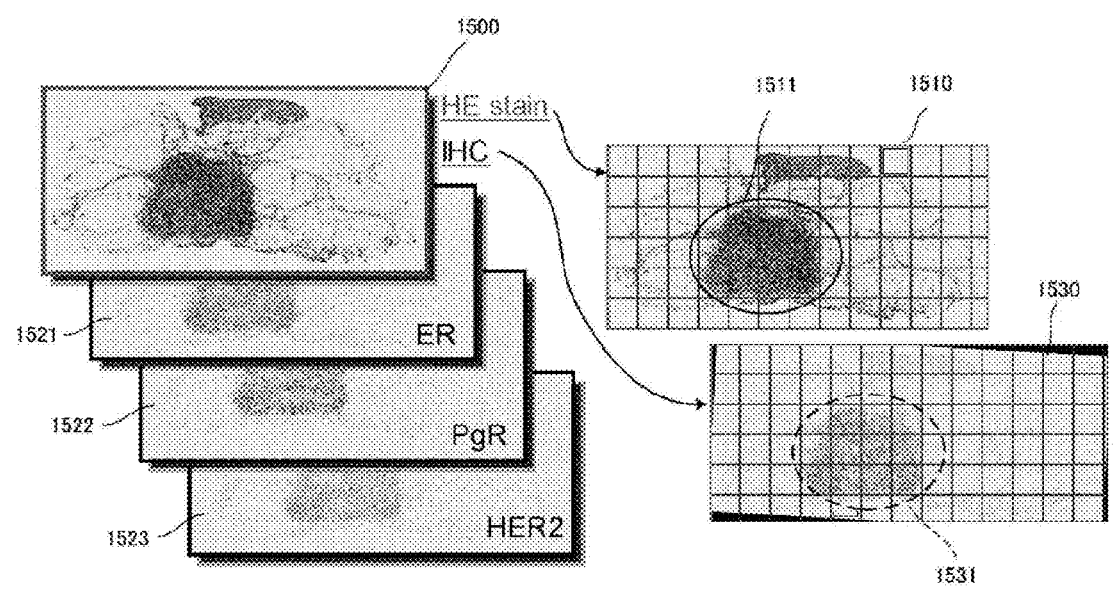
FIG. 15 is a figure showing superimposition of a selected area according to the fourth embodiment of the present invention.

When the pathological image diagnosis support apparatus 200 receives a tissue sample image of the same biological tissue stained by another staining method, the sequence is shifted to a sequence S1409. In the sequence S1409, the position of the mark stored in the sequence S1401 is read out. In a sequence S1411, the tissue sample image with the mark read from the HE-stained slide with the mark is aligned with the tissue sample image without the mark read from the IHC-stained slide without a mark. FIG. 15 schematically shows the alignment. In FIG. 15, the numeral 1500 indicates a HE-stained tissue sample image, the numeral 1521 indicates an IHC-stained ER tissue sample image, the numeral 1522 indicates an IHC-stained PgR tissue sample image, and the numeral 1523 indicates an IHC-stained HER2 tissue sample image. The numeral 1510 indicates a HE-stained tissue sample image, and the numeral 1511 indicates a mark in the tissue sample image with the mark. The numeral 1530 indicates an IHC-stained tissue sample image. The alignment is performed by pattern matching such as rotating an image, for example. The alignment is described in detail in the patent document 1 and the like and can be performed appropriately by those skilled in the art.

When the number of cancer cells in each selected area is counted in a sequence S1413, the mark 1511 put on the HE-stained tissue sample image 1510 can also serve as a mark 1531 of the IHC-stained tissue sample image 1530.

In a sequence S1415, the counted number of cancer cells is sent to the client PC220. At that time, display data of the selected area is sent in addition to the counted number of cancer cells.

Other Embodiments

The embodiments of the present invention are described in detail above. The scope of the present invention encompasses any system and apparatus obtained by combining characteristics of the embodiments.

The present invention may be applied to a system composed of a plurality of units or a single unit. The present invention is applicable also in the case where the control program for achieving the functions of the embodiments is supplied from a system or apparatus directly or remotely. Therefore, the scope of the present invention encompasses a control program installed in a computer so as to achieve functions of the present invention, a medium storing the control program, and a WWW server from which the control program is downloaded.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

This application is based upon and claims the benefit of priority from Japanese patent application No. 2010-223050, filed on Sep. 30, 2010, the disclosure of which is incorporated herein in its entirety by reference.

EXPLANATION OF REFERENCE NUMERALS 100 information processing apparatus
110 acquisition section (acquisition unit)
120 counting section (counting unit)
150 tissue sample image
151 mark
152 selected area (focus area)
155 image data
200 pathological image diagnosis support apparatus (information processing apparatus)
201 communication control section (receiving unit, sending unit)
202 image storage section (acquisition unit)
203 mark recognition section (mark recognition unit)
204 mark position storage section (mark position storage unit)
205 mark-specified region selection section (selection unit)
206 specified region dividing section (dividing unit)
207 cancer cell counter (counting unit)
208 display data generation section (display data generation unit)
220 client PC (input terminal, display terminal)
221 color scanner (input terminal)
230 pathological image diagnosis center (display terminal)
240 network
250 information processing system
410 CPU
420 ROM
430 RAM
431 image data to be processed
432 display data
433 program execution region
440 storage
441 diagnosis support information
442 various parameters
443 various programs
451 tissue sample image with mark received via communication control section 201
452 mark image recognized from tissue sample image with mark
453 image of one selected area selected from received tissue sample image
461 selected area-mapped image obtained by mapping selected area into received tissue sample image
462 the first selected area image of the first selected area
463 the first cell count value which is the counted number of cancer cells with each staining intensity in the first selected area image
471 received tissue sample image
472 position and size of selected area as partial region selected from tissue sample image
473 the count value relating to cancer cells in selected area
474 processed display data stored so as to be searchable by tissue sample image, patient, case, and the like
481 closed curve extraction parameter for extracting put mark or added mark on tissue sample image
482 closed curve formation parameter for distinguishing and complementing
483 mesh size parameter
491 diagnosis support program for supporting diagnosis
492 mark extraction program for extracting mark on tissue sample image and recognizing selected area (for executing S520 of FIG. 5)
493 cell count program for counting the number of cells with each staining intensity in image of selected area (for executing S540 of FIG. 5)
494 mesh division program for dividing selected area into meshes
600 tissue sample image with mark
601 mark which is closed curve enclosing region 602
602 region (selected area) in which user desires to count the number of cancer cells
700 tissue sample image with marks
701 rectangular mark
702 to 704 marks which are closed curves
800 selected area-mapped image
801 closed curve extracted from mark
802 selected area
900 tissue sample image of selected area
901 the counted number with each staining intensity
1000 display screen
1001 enlarged tissue sample image of one selected area
1002 reduced-size image of selected area
1003 thumbnail image of tissue sample image
1004 thumbnail images of five selected areas, each including bar-graph 1010 bar-graph according to selected area
1011 region indicating the number of cells with "strong" staining intensity
1012 region indicating the number of cells with "weak" staining intensity
1013 region indicating the number of cells with "none" of staining intensity
1100 display image
1101 tissue sample image
1102 reduced-size image of selected area
1103 thumbnail image of tissue sample image
1104 thumbnail images of five selected areas, each including bar-graph
1105 marks of selected areas in each of which the number of cells has been counted
1106 marks of added selected areas
1300 display image
1301 mark enclosing selected area
1302 mesh regions in divided selected area
1500 HE-stained tissue sample image
1510 HE-stained tissue sample image
1511 mark of tissue sample image with mark
1521 IHC-stained ER tissue sample image
1522 IHC-stained PgR tissue sample image
1523 IHC-stained HER-2 tissue sample image
1530 IHC-stained tissue sample image
1531 mark of tissue sample image 1530

The invention claimed is:

1. An information processing apparatus comprising:
an acquisition unit configured to acquire image data obtained by reading a tissue sample image obtained by putting a mark specifying a selected area on an image obtained by immunostaining and then imaging a biological tissue; and
a counting unit configured to count a number of cancer cells in the selected area specified by the mark, based on the image data of the tissue sample image acquired by the acquisition unit, and having:
a dividing unit configured to divide a focus area of stained positive cells indicated by the mark into a plurality of small areas of meshes; and
a small area selection unit configured to select a small area from the plurality of small areas of meshes, wherein a number of cells with each staining intensity, contained in the small area selected by the small area selection unit, is counted;
whereby a diagnosis based on the tissue sample image is supported, wherein the counting unit is further configured to count a second number of cancer cells in at least one of the small areas of meshes in response to a user selection of the at least one of the small areas of meshes from a display of the small areas of meshes superimposed on the focus area within the mark;
wherein the counting unit is further configured to count the second number of cancer cells in response to the user selection of the small areas of meshes received after the counting unit counts the number of cancer cells in the selected area specified by the mark.

2. The information processing apparatus according to claim 1, wherein
the counting unit further comprises:
a display unit configured to display the plurality of small areas of meshes into which the focus area of the stained positive cells is divided by the dividing unit; and
an accepting unit configured to accept a selection instruction of selecting a small area contained in the plurality of small areas of meshes which are displayed by the display unit from a user, and
the number of cells with each staining intensity, contained in the small area specified by the selection instruction is counted.

3. The information processing apparatus according to claim 1, wherein
the selected area is divided into the plurality of small areas of meshes using a mesh size parameter.

4. The information processing apparatus according to claim 1, wherein the acquisition unit is further configured to detect the mark according to a combination of a closed curve extraction parameter and a closed curve formation parameter.

5. The information processing apparatus according to claim 4, wherein the closed curve extraction parameter is a predetermined color of the mark and the closed curve formation parameter is a predetermined shape of the mark.

6. The information processing apparatus according to claim 4, wherein the acquisition unit is further configured to align the image data of the tissue sample image comprising the mark with another image data of another tissue sample image without the mark,
wherein the another tissue sample image is stained by a second stain which is different from a first stain which stains the tissue sample image.

7. The information processing apparatus according to claim 1, wherein the dividing unit is further configured to divide the focus area into the plurality of small areas of meshes after the counting unit counts the number of cancer cells in the selected area specified by the mark.

* * * * *